(12) United States Patent
Wilson et al.

(10) Patent No.: US 8,520,918 B2
(45) Date of Patent: Aug. 27, 2013

(54) MEDICAL DIAGNOSTIC IMAGE CHANGE HIGHLIGHTER

(76) Inventors: Kelce S Wilson, Murphy, TX (US); Susan M. Gaschke, Tigard, OR (US)

( * ) Notice: Subject to any disclaimer, the term of this patent is extended or adjusted under 35 U.S.C. 154(b) by 625 days.

(21) Appl. No.: 12/772,216

(22) Filed: May 2, 2010

(65) Prior Publication Data

US 2010/0208967 A1    Aug. 19, 2010

(51) Int. Cl.
*G06K 9/00*    (2006.01)

(52) U.S. Cl.
USPC ......................................................... 382/128

(58) Field of Classification Search
USPC ......................................................... 382/128
See application file for complete search history.

(56) References Cited

U.S. PATENT DOCUMENTS 6,901,277 B2 * 5/2005 Kaufman et al. ............. 600/407
7,496,242 B2 * 2/2009 Hunt ............................ 382/293

OTHER PUBLICATIONS

Office of Geospatial-Intelligence Management, "National System for Geospatial Intelligence, Geospatial Intelligence (GEOINT) Basic Doctrine, Publication 1-0", p. 14, Sep. 2006 by National Geospatial Intelligence Agency, USA, p. 14.
"New Products", http://www.gisuser.com.au/POS/NEW_PROD-UCTS/11_09_NP.html, pp. 1-2, printed on Jul. 16, 2009, dated 2006 by South Pacific Science Press International P/L, Australia.
ITT Visual Information Solutions, "Workflow Tools in ENVI, Whitepaper", p. 6, obtained by Applicant on Jul. 16, 2009, date unknown.

\* cited by examiner

*Primary Examiner* — Michelle Le
(74) *Attorney, Agent, or Firm* — Kelce S. Wilson (57) ABSTRACT

Systems and methods are disclosed which enable more accurate examination of medical diagnostic images, for example x-ray, ultrasound and magnetic resonance imaging (MRI) images. The systems and methods highlight anomalies that have changed between the collection times of two or more diagnostic images, and can also provide objective scoring of the degree of change.

18 Claims, 8 Drawing Sheets

MEDICAL DIAGNOSTIC IMAGE CHANGE HIGHLIGHTER

TECHNICAL FIELD

The invention relates generally to image rendering. More particularly, and not by way of any limitation, the present application relates to generating an image that highlights differences between medical diagnostic images.

BACKGROUND

When a dentist is attempting to determine whether an apparent anomaly in a patient's recent dental x-ray image merits further investigation and treatment, the dentist will often compare the recent x-ray image with one taken at a prior time. This is typically accomplished by placing both x-ray images within the dentist's field of view, perhaps on a single computer monitor, but as separate images. The dentist then alternates focus between the two images, in order to ascertain whether the apparent anomaly is new, has worsened over time, or else has remained fairly unchanged. If the apparent anomaly is new, or has worsened over time, the dentist may suspect the recent formation of a cavity or other damage to the patient's teeth.

Other medical professionals may perform a similar procedure using ultrasound images, magnetic resonance imaging (MRI) images, or other medical diagnostic images, to diagnose other medical conditions. The professionals use their own judgment, which can vary according to experience and other factors, to determine whether the amount of change is problematic, based on the time difference between when the different images were collected. Thus, current change analysis is subjective, and can potentially be inconsistent.

Unfortunately, there are multiple shortcomings with the above procedure: There is a possibility that a new anomaly in a diagnostic image may be missed by the medical professional, and also there is no objective score to quantify differences between the images. These problems can result in accusations of sub-standard care by medical malpractice attorneys if a patient later claims that a developing medical problem was not identified in the images.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Systems and methods are disclosed which enable more accurate examination of medical diagnostic images, for example x-ray, ultrasound and magnetic resonance imaging (MRI) images. This is accomplished by generating a comparison image that highlights changes for medical professionals, such as doctors and dentists, between two medical diagnostic images that were collected at different times. Embodiments of the disclosed systems and methods highlight anomalies that have changed between the collection times of two or more diagnostic images, and can also optionally provide objective scoring of the degree of change.

Figure 1:
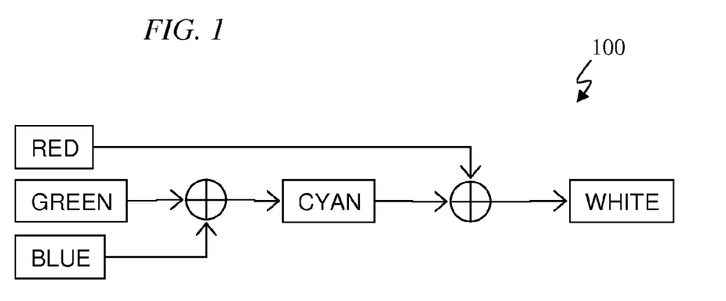
FIG. 1 illustrates color mixing.

FIG. 1 illustrates a color mixing diagram 100, explaining how white light can be created by combining various different colors. For example, a combination of red, green and blue can create white, if the red, green and blue components are properly balanced. Combinations of two of the three colors can create other colors. As illustrated, green and blue are combined to create cyan.

Figure 2:
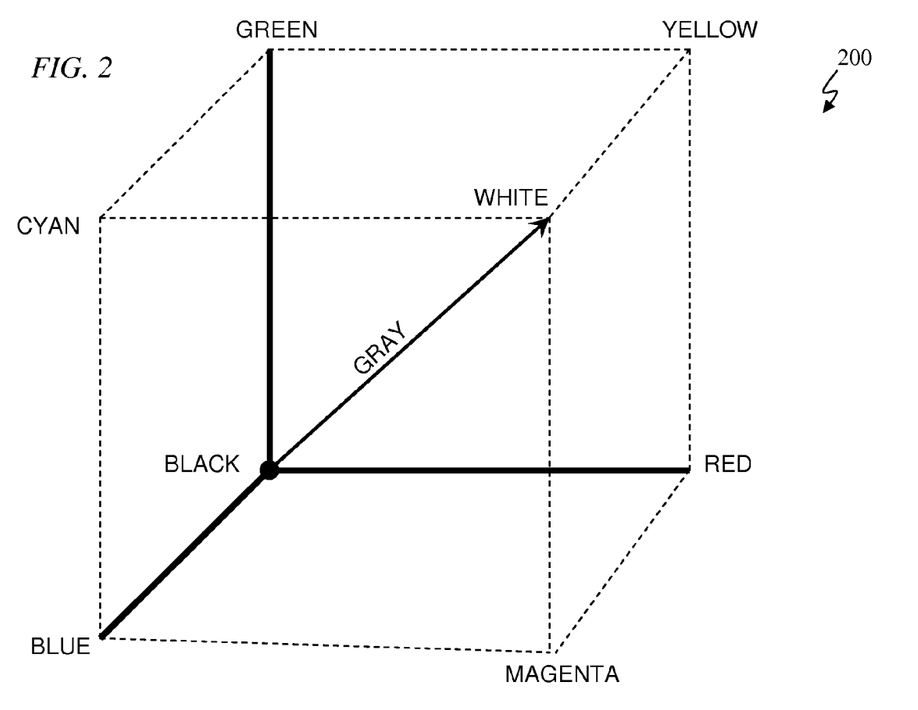
FIG. 2 illustrates a 3-dimensional color cube.

FIG. 2 illustrates a 3-dimensional color cube 200, which also represents color mixing options. Red is illustrated as an axis of the cube, as are green and blue. Any specific color can be achieved simply by mixing a selected intensity of the red, green and blue color components. For cube 200, the intensity of a particular color component is represented as a distance away from black, along one of the color component axes. To explain the color cube, the black corner can be addressed first. The absence of any color, which occurs when all of red, green and blue are set to zero intensity, is black. Mixing a full intensity of red and green, but with no blue, creates yellow. Adding a full intensity of blue to yellow creates white. Mixing a full intensity of green and blue, but with no red, creates cyan. Adding a full intensity of red to cyan creates white. Mixing a full intensity of red and blue, but no green, creates magenta. Adding a full intensity of green to magenta creates white.

For 24-bit color bitmaps, which are common in computer graphics, color intensity is often scaled between 0 and 255, with 255 representing full intensity. Therefore, with a 24-bit color bitmap image, a pixel having a 255 level of each of red, green, and blue is a white pixel. A pixel having equal red, green and blue levels below 255 is gray. Therefore, the color gray can be considered to be a color axis running diagonal from the black corner of color cube 200, in a straight line to the most distant corner of the cube, which is the white corner.

Figure 3:
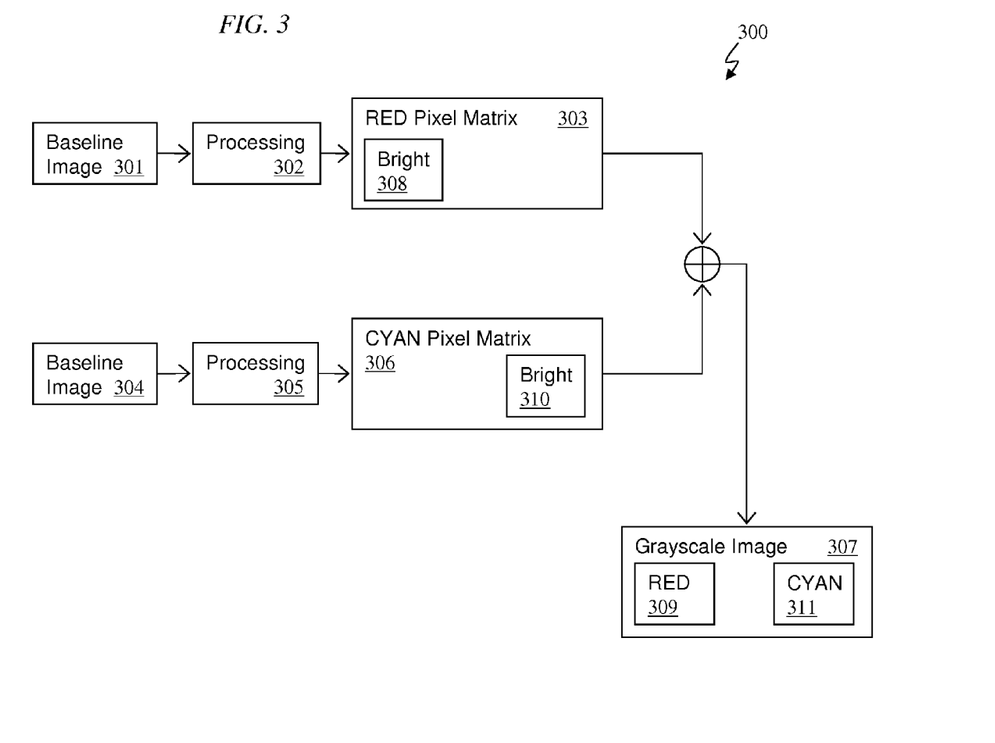
FIG. 3 illustrates a block diagram for generating a medical diagnostic comparison image.

FIG. 3 illustrates a block diagram 300 for generating a medical diagnostic comparison image 301. A baseline medical diagnostic image 301, which is received into a computer readable medium, is processed according to a processing method 302, to create a baseline pixel matrix 303, wherein baseline pixel matrix 303 represents an intensity of pixels in at least a portion of baseline medical diagnostic image 301. A baseline medical diagnostic image 304, which is received into a computer readable medium, is processed according to a processing method 305, to create a baseline pixel matrix 306, wherein baseline pixel matrix 306 represents an intensity of pixels in at least a portion of baseline medical diagnostic image 304. Processing methods 302 and 305 may include adjusting any of rotation, magnification, horizontal displacement, vertical displacement, and intensity.

Creating a comparison image 307 can be accomplished by using baseline pixel matrix 303 to provide red pixel intensities and baseline pixel matrix 306 to provide cyan pixel intensities. To the extent that corresponding pixels in matrices 303 and 306 are equal, comparison image 307 will be grayscale. There may be some differences among the pixel intensity values, but if the differences are a relatively minor percentage of the intensity values, comparison image 307 will be reasonably close to gray.

However, as illustrated, there is a bright region 308, within baseline pixel matrix 303, in which pixel intensities exceed the intensity of corresponding pixels in the baseline pixel matrix 306. Because the pixel intensities are imbalanced, the corresponding pixels in comparison image 307 will have a colored hue. Since baseline pixel matrix 303 provides the red color information, the hue will be red. This is indicated as red-hued region 309, within comparison image 307. Similarly, there is a bright region 310, within baseline pixel matrix 306, in which pixel intensities exceed the intensity of corresponding pixels in the baseline pixel matrix 303. Because the pixel intensities are imbalanced, the corresponding pixels in comparison image 307 will have a colored hue. Since baseline pixel matrix 306 provides the cyan color information, the hue will be cyan. This is indicated as cyan-hued region 311, within comparison image 307.

For the case in which two identical baseline images are used in the process, the output will be a purely grayscale image. However, if the pixel intensities for most of the corresponding pixels in each of matrices 303 and 306 are close enough that comparison image 307 appears gray to a human observer, with some regions of red or cyan hue, as noted above, comparison image 307 will only be a predominantly grayscale image.

Figure 4:
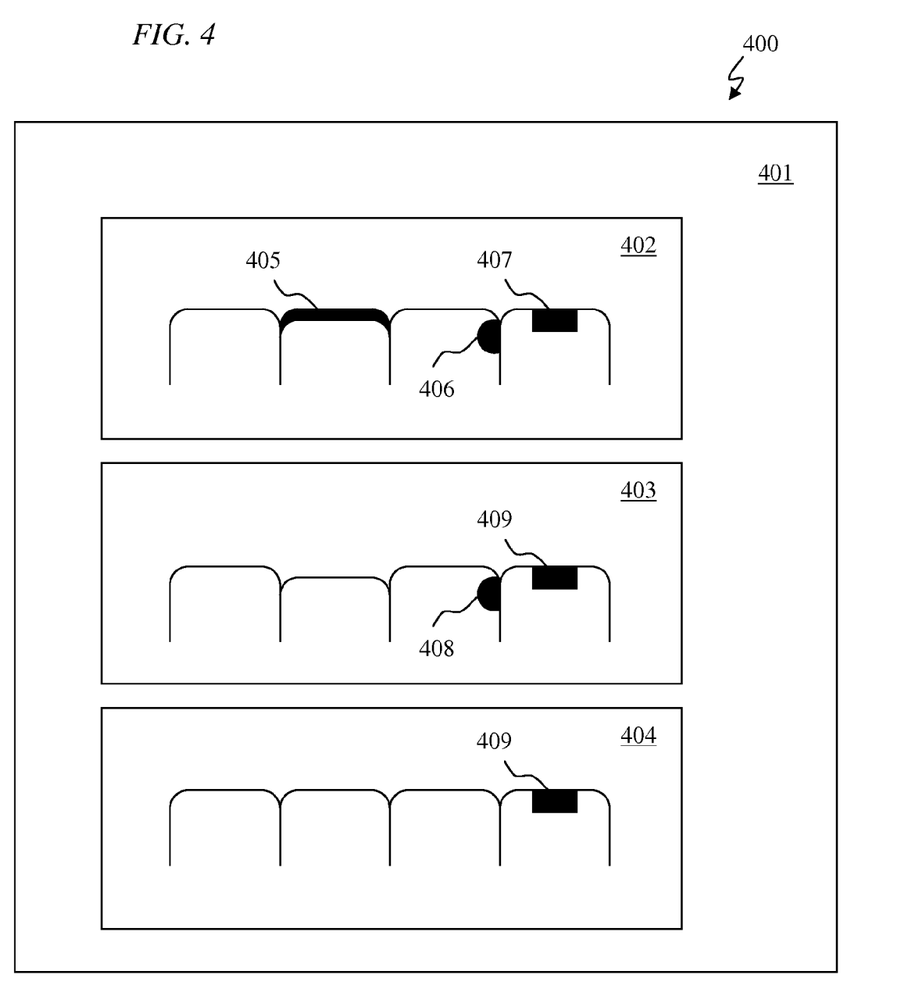
FIG. 4 illustrates a set of baseline medical diagnostic images and a comparison image on a display.

FIG. 4 illustrates a display 400, having a video display screen 401, which is showing a comparison image 402, a baseline medical diagnostic image 403 and another baseline medical diagnostic image 404. A medical professional may wish to see not only comparison image 402, but also baseline medical diagnostic images 403 and 404, simultaneously with comparison image 402, in order to diagnose changed medical conditions for a patient. In one example use, baseline medical diagnostic image 403 is the currently-collected image, perhaps collected just minutes or seconds prior to the creation of comparison image 402, and baseline medical diagnostic image 404 is an older image, perhaps collected during a patent's prior visit to the medical professional. In some uses, baseline medical diagnostic image 404 could have been in the patient's medical history, collected by a different medical professional and acquired over a computer network. Either originally-collected images could be used, processed images from any stage of the registration process, zoomed-in portions, or any combination. Although three images are illustrated, it should be understood that a different number of images could be used.

As illustrated, comparison image 402 highlights a region 405 of tooth wear, which can be identified using dental x-ray images. Comparison image 402 also highlights a region 406 that indicates a cavity in one of the patient's teeth. Region 407, which is a region of abnormal intensity, corresponds to a dental filling, and should be fairly close to gray. However, regions of abnormal brightness or darkness in baseline images may be subject to tinting in the comparison image, due to differences in the collections of the images at different times. These differences may include the use of different equipment or different imaging angles. One reason that the medical professional may wish to see the images simultaneously is to be able to ascertain that region 406 has a corresponding abnormal region 408 within diagnostic image 403, but not diagnostic image 404, and that region 407 has corresponding abnormal regions 409 within both diagnostic image 403 and diagnostic image 404.

From a quick scan of comparison image 402 and baseline medical diagnostic images 403 and 404 on screen 401, a dentist can quickly ascertain tooth wear, the formation of a new cavity, and identify a filling as predating the earlier image 404.

In order to form a useful comparison image, though, two or three baseline images should be as close to identical as practical, so that the largest and most brightly hued regions correspond to meaningful differences, such as changed medical conditions, rather than differences in image collections. Since it is possible that the baseline medical diagnostic images were collected differently, adjustments may be needed for rotation, magnification, horizontal displacement, vertical displacement, and intensity—both average and extremes. Such adjustments are known in the art, and may use averaging, edge detection, and interpolation. In many cases, the individual steps of minimizing differences between two images may be iterative. For example, small adjustments can be made in rotation, then magnification, and then rotation may be adjusted again. In some embodiments, such adjustments can be accomplished under human control, with a comparison image made after each adjustment, and with the human attempting to minimize the hued regions in the comparison image. Since an objective scoring method is described later, the image alignment process can be automated, with the controlling algorithm iterating adjustments and scoring in an attempt to minimize the objective difference score.

Figure 5:
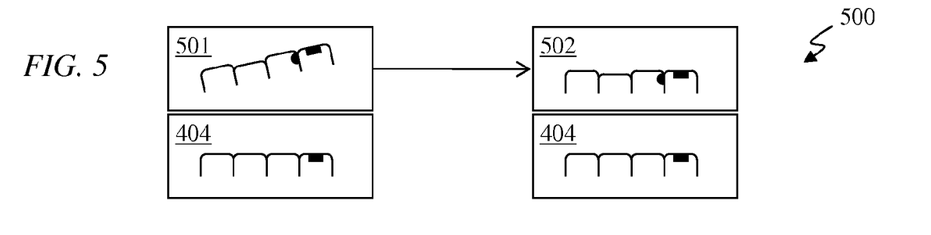
FIG. 5 illustrates a rotation adjustment of one baseline medical diagnostic image relative to another baseline medical diagnostic image.

FIG. 5 illustrates a rotation adjustment of baseline medical diagnostic image 501 relative to baseline medical diagnostic image 404, to produce adjusted baseline medical diagnostic image 502 in process 500. In some embodiments, adjusting a rotation of a baseline pixel matrix comprises calculating a pixel matrix using one of a nearest neighbor method, a linear interpolation method, and a polynomial interpolation method; and replacing the initial baseline pixel matrix with the new pixel matrix. This new pixel matrix forms the pixel intensity information for adjusted baseline medical diagnostic image 502. Rotation of one image relative to another, in order to automatically align the images, is known in the art and is commonly performed in computer graphics functions. In some embodiments, a human could control the rotation process. Although rotation of only one image is illustrated, it should be understood that either or both images could be rotated.

Figure 6:
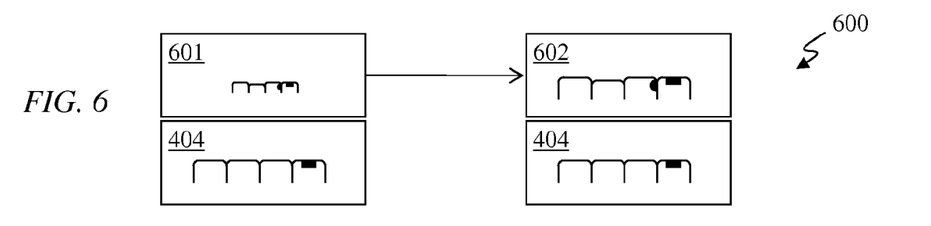
FIG. 6 illustrates a magnification adjustment of one baseline medical diagnostic image relative to another baseline medical diagnostic image.

FIG. 6 illustrates a magnification adjustment of baseline medical diagnostic image 601 relative to baseline medical diagnostic image 404, to produce adjusted baseline medical diagnostic image 602 in process 600. In some embodiments, adjusting a magnification of a baseline pixel matrix comprises calculating a pixel matrix using one of a nearest neighbor method, a linear interpolation method, and a polynomial interpolation method; and replacing the initial baseline pixel matrix with the new pixel matrix. This new pixel matrix forms the pixel intensity information for adjusted baseline medical diagnostic image 602. Adjustment of image magnification of one image relative to another, in order to automatically align the images, is known in the art and is commonly performed in computer graphics functions. In some embodiments, a human could control the magnification adjustment process. Although magnification adjustment of only one image is illustrated, it should be understood that either or both images could be adjusted for magnification.

Figure 7:
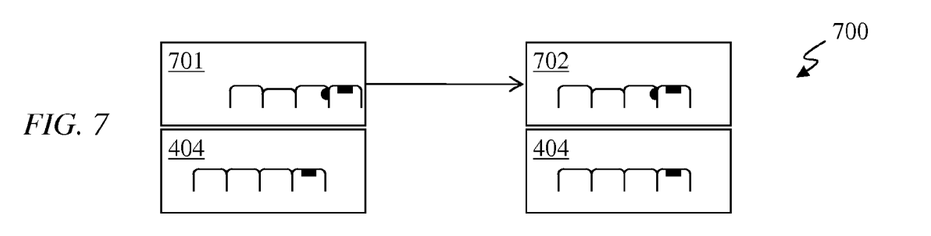
FIG. 7 illustrates a horizontal displacement adjustment of one baseline medical diagnostic image relative to another baseline medical diagnostic image.

FIG. 7 illustrates a horizontal displacement adjustment of baseline medical diagnostic image 701 relative to baseline medical diagnostic image 404, to produce adjusted baseline medical diagnostic image 702 in process 700. In some embodiments, adjusting a displacement of a baseline pixel matrix comprises generating a new pixel matrix based on a cropped version of the baseline pixel matrix; and replacing the baseline pixel matrix with the new pixel matrix. This new pixel matrix forms the pixel intensity information for adjusted baseline medical diagnostic image 702. In some embodiments, both images will require cropping. Displacement adjustment of one image relative to another, in order to automatically align features within the images, is known in the art and is commonly performed in computer graphics functions. In some embodiments, a human could control the translation and cropping process. Although adjustment of only one image is illustrated, it should be understood that either or both images could be adjusted.

Figure 8:
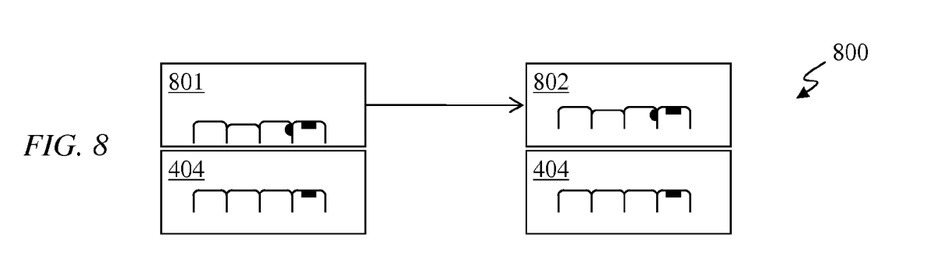
FIG. 8 illustrates a vertical displacement adjustment of one baseline medical diagnostic image relative to another baseline medical diagnostic image.

FIG. 8 illustrates a vertical displacement adjustment of baseline medical diagnostic image 801 relative to baseline medical diagnostic image404, to produce adjusted baseline medical diagnostic image 802 in process 800. Although adjustment of only one image is illustrated, it should be understood that either or both images could be adjusted.

Figure 9:
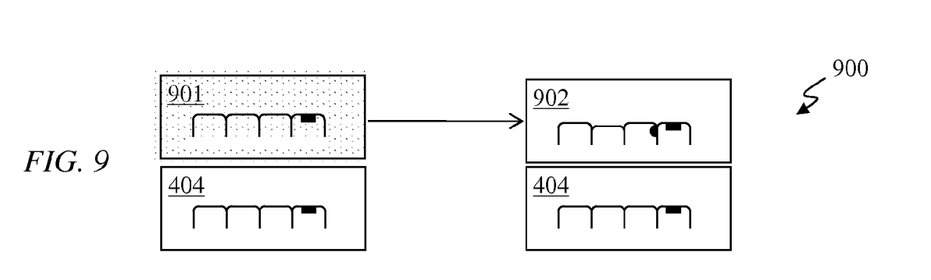
FIG. 9 illustrates an intensity adjustment of one baseline medical diagnostic image relative to another baseline medical diagnostic image.

FIG. 9 illustrates an intensity adjustment of baseline medical diagnostic image 900 relative to baseline medical diagnostic image 404, to produce adjusted baseline medical diagnostic image 902 in process 700. In some embodiments, adjusting pixel intensity comprises adjusting average intensity, minimum intensity, maximum intensity, contrast, and various combinations. Adjustments may be linear or non-linear. It should be understood that the afore-mentioned processes could be performed on image pixels directly, while they reside within computer memory formatted as image color information, or else the pixel intensities could be copied into normal matrices, operated upon, and then these matrices could be used to create new images or replace the pixel values within existing images. In some embodiments, a human could control the intensity adjustment process. Although adjustment of only one image is illustrated, it should be understood that either or both images could be adjusted. Together, FIGS. 5 through 9 illustrate an exemplary image registration process.

Figure 10:
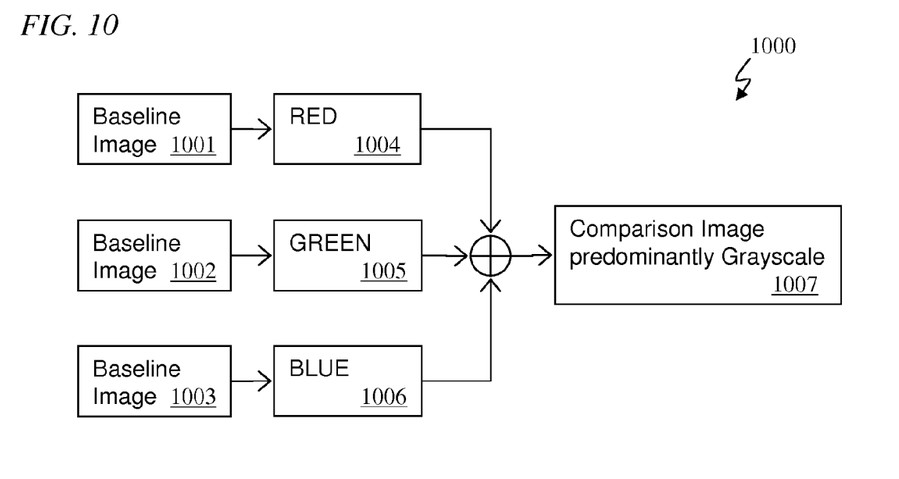
FIG. 10 illustrates another block diagram for generating a medical diagnostic comparison image.

FIG. 10 illustrates another block diagram 1000 for generating a medical diagnostic comparison image 1007. Baseline images 1001, 1002 and 1003 are used to create red matrix 1004, green matrix 1005 and blue matrix 1006, respectively. The formation of an image in this manner creates a three-color multi-view, rather than a two-color multi-view (2CMV), which was illustrated in FIG. 3. It should be noted that some medical professionals may prefer that the pixel intensities of the constituent color matrices are not enhanced in regions of pixel intensity differences among the multiple images. However, some medical professionals may prefer that pixel intensity differences in the hued regions, in which the pixel intensities of the color components differ, be exaggerated, to more clearly highlight the color differences. One method of doing this is to have a non-linear mapping of pixel intensities, such that if R−G=X for a pixel (R is the red intensity, G is the green intensity), then for that pixel R is replaced with R+X/2 and G with G−X/2. This would make a reddish pixel more deeply red, or a greenish pixel more brightly green.

Other color enhancement or difference exaggeration transforms could be used, such as multiplicative transforms. Color difference exaggeration can also be used between red and cyan colors for two-color systems. Exaggerations of differences could be adjustable, such as by a user inputting a preference to vary color enhancement though a graphical user interface (GUI). This can permit a medical services provider to tailor color enhancement to a preference, although such a visual display preference should not affect any objective difference scoring. That is, objective scoring could be accomplished with a consistent difference calculation scheme.

In block diagram 1000, the generation process for comparison image 1007 includes receiving a third baseline medical diagnostic image into a computer readable medium; creating a third baseline pixel matrix, wherein the third baseline pixel matrix represents an intensity of pixels in at least a portion of the third baseline medical diagnostic image; adjusting a rotation of the third baseline pixel matrices relative to the other baseline pixel matrices; adjusting a magnification of the third baseline pixel matrices relative to the other baseline pixel matrices; adjusting a displacement of the third baseline pixel matrices relative to the other baseline pixel matrices; and adjusting an intensity of at least a portion of the third baseline pixel matrices relative to corresponding portions of the other baseline pixel matrices. Creating comparison image 1007 comprises creating a predominantly intensity-only image with the third baseline pixel matrix providing a third color information. If about 80% or more of the pixels have the differing colors intensities within approximately 10% of each other, the comparison image will be predominantly grayscale. In some embodiments, a different intensity difference could be used, including either absolute differences or another percentage difference.

Figure 11:
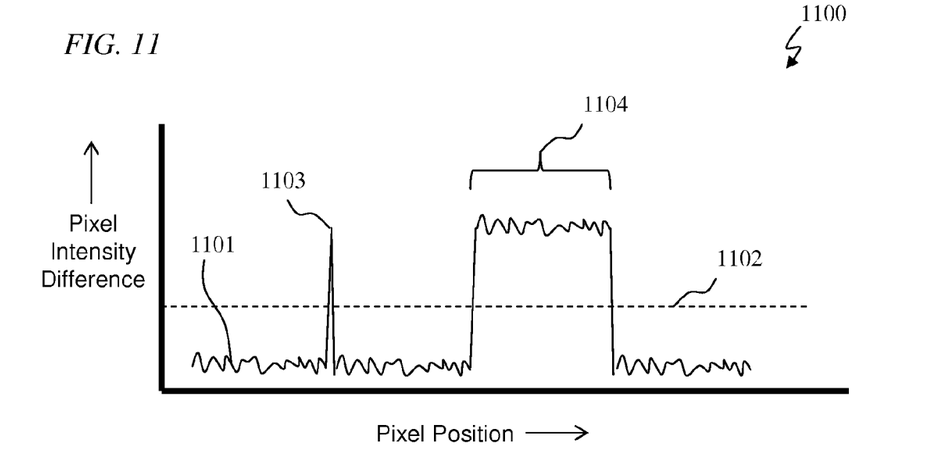
FIG. 11 illustrates a plot of pixel intensity difference values along a row or column of a pixel intensity matrix.

FIG. 11 illustrates a plot 1100 of pixel intensity difference values along a row or column of a pixel intensity matrix. Plotted line 1101 could be an absolute value or a signed value, based on whether a single threshold is used for scoring or whether positive and negative thresholds are used. Plotted line 1101 is the value of the pixel intensity difference between corresponding pixels in different color matrices, for example matrices 303 and 306 of FIG. 3, as a function of pixel position. The horizontal axis, "Pixel Position", represents a matrix index number, and could be either a row or a column index. The vertical axis, "Pixel Intensity Difference" is the value of the difference. A threshold 1102 is illustrated, which could be either an absolute number, or could represent a percentage difference, for example 10% of the maximum pixel intensity in either of the images.

Plotted line 1101 exceeds threshold 1102 in two places. One is anomalous point 1103, which is only a single pixel. Anomalous point 1103 could be due to measurement error or electrical noise within the imaging system. Anomalous point 1103 could be removed from consideration, and eliminated as a distraction to a medical professional by using a moving average window over plotted line 1101. Anomaly suppression in images is well-known in the art, and may be added to many of the process described herein.

Difference region 1104 is an area in which plotted line 1101 exceeds threshold 1102 over an extended length. If pixels within difference region 1104 were also within a similar, extended difference region in the orthogonal "Pixel Position" direction, then such pixels would be within a 2-dimensional difference region. The remaining smaller peaks and valleys in plotted line 1101 represent image noise.

Figure 12:
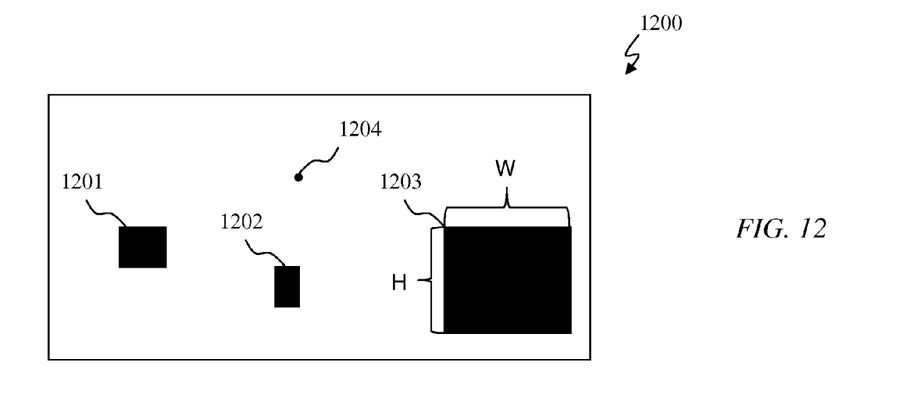
FIG. 12 illustrates scoring criteria for a medical diagnostic comparison image.

FIG. 12 illustrates scoring criteria for a medical diagnostic comparison image 1200. Comparison image 1200 comprises three regions, 1201, 1202 and 1203. The height, H, and width, W, of region 1203 are indicated, although a difference region could be any geometric shape, including both convex and concave shapes. Comparison image 1200 also includes anomalous pixel 1204. Relating FIG. 12 to FIG. 11, plotted line 1101 represents a column of pixel intensity difference values that extend from the top to the bottom of comparison image 1200, through anomalous pixel 1204 and region 1202. Anomalous point 1103 corresponds to anomalous pixel 1204, and difference region 1104 extends vertically across region 1202, in this exemplary relation of the hypothetical data sets illustrated using FIGS. 11 and 12.

A method of scoring a comparison image may include comparing a region of pixel intensity difference to both an average intensity difference threshold and also a minimum dimension threshold. The dimension threshold could include multiple criteria, such as minimum span in orthogonal directions, as well as minimum area. Responsive to the region of pixel intensity difference meeting or exceeding the average intensity difference threshold and the minimum dimension threshold, the system could cause an alert to draw a medical professional's attention to the extent of the differences within a comparison image. However, such an alert should be delayed until the comparison image formation process has produced the best alignment of the baseline images, in order to avoid causing false alarms if the difference regions are due predominantly to misalignment of the baseline images. Other alert criteria can also be used, such as a dimension of a difference region that meets or exceeds an average intensity difference threshold; a count of difference regions that meet or exceed an average intensity difference threshold and a minimum dimension threshold; and a time difference associated with the images. For example, if the baseline images had been created years apart, more differences could be expected than if the images had been created only a few months apart.

Scoring of differences can also be performed without the rendering of a color image, such as using the baseline images as input matrices to a scoring process without assigning color significance to either matrix. A difference score can be calculated for a portion of an image such as a region of interest, either selected manually by a user, or automatically by performing a segmentation process on the image. The same region of interest or a different region of interest may be included in the displayed image or images. One advantage of scoring only a subset of the image views is that noise and spurious results in background areas can be excluded. Examples of regions of interest can include a specific tooth, a set of teeth, a specific bone or set of bones, specific organs, and subsections of these examples. There is no need for a scored section to be rectangular, but instead could be defined by any closed curve, whether purely convex or having concavities. One possible scoring algorithm is Score=$(1/N)$ *SUM$((T((I_{1RC}-I_{2RC}),t))^E)$, where N is the number of pixels included in the scoring region used in the SUM summation, T is a threshold function, $I_{1RC}$ is the processed pixel intensity value of image 1 at row position R and column position C, $I_{2RC}$ is the processed pixel intensity value of image 2, t is a threshold value, and E is an exponential factor. The $(1/N)$ normalizes the score, and $T(A,t)$ returns 0 if A<t and A otherwise. For E>1, the score will be weighted most heavily by large differences, even if only over a relatively small number of pixels. For E<1, the effect of a few large differences will be muted in the entire score. It should be understood that it is merely an exemplary scoring algorithm, and that other scoring algorithms may be used.

Figure 13:
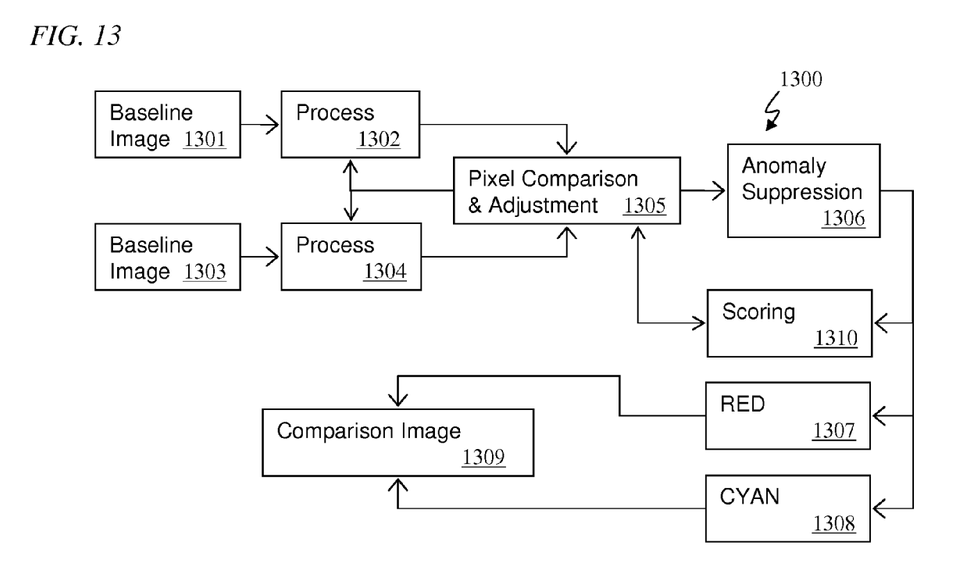
FIG. 13 illustrates another block diagram for generating a medical diagnostic comparison image.

FIG. 13 illustrates another block diagram 1300 for generating a medical diagnostic comparison image 1309, which may be displayed for a medical professional simultaneously with at least a portion of baseline medical diagnostic image 1301, at least a portion of baseline medical diagnostic image 1302, or both. Baseline medical diagnostic image 1301 is processed according to the logic contained in process module 1302, and baseline medical diagnostic image 1303 is processed according to the logic contained in process module 1304. The processed results, which include rotation, magnification, displacement, and intensity adjustments, are sent to pixel comparison and adjustment control module 1305. Module 1305 passes the results to anomaly suppression module 1306, which is then used to create red matrix 1307 and cyan matrix 1308. Red matrix 1307 and cyan matrix 1308 are combined to create comparison image 1309.

A scoring module 1310 is illustrated as coupled to both pixel comparison and adjustment control module 1305 and the output of anomaly suppression module 1306. Scoring module 1310 can calculate objective scores based on the pixel differences. The score could be a single number or else a weighted composite score that included the total area of all difference regions and a total count of difference regions exceeding some minimum dimensions. Scoring module 1310 can be used for both feedback to enable automated fine-tuning of the baseline image adjustments in process modules 1302 and 1304, as well as for final scoring and generating alerts. Final scoring, causing alerts for high scores, and pixel difference exaggeration to more brightly highlight any differently-hued regions, should generally occur after the best possible fine-tuning of the baseline image alignment has been accomplished.

For an automated image alignment process, after receiving the baseline images, a trial adjustment can be accomplished, perhaps by using an edge detection process and feature extraction. Fine-tuning can be achieved by attempting to minimize a difference score, which could be a composite score that included the total area of all difference regions and a total count of difference regions exceeding some minimum dimensions or area. The score minimization could be a trial and error process, could use genetic algorithms, or could be predictive, using sensitivity analysis, in order to predict the optimum adjustments by comparing the change after multiple attempts. For example, an initial score is known for the initial set of image adjustment parameters, including displacement, intensity, rotation, magnification, and perhaps another parameter. A particular parameter, identified as parameter P, is selected for trial adjustment. It is changed, and a new score is found. Based on the set of known scores, a new value of P is selected that should reduce the score. One way this can be accomplished is by treating the set of scores as a function that is dependent upon P. This new value of P is tried, and the process repeats until the score cannot be lowered merely by changing P. Then another parameter, Q, is chosen for alteration. When the score is again lowered to a minimum level for a particular P and Q, the next parameter is chosen for alteration. When all parameters have been individually adjusted, the process starts with P again, until no more reduction is possible. Sensitivity analysis is known in the art for minimizing a cost function, difference score, or other metric, as a function of multiple input parameters. Although an iterative process has been described for individual parameter adjustment, multiple, simultaneous parameter adjustments for minimizing a cost function are also well-known in the art.

Figure 14:
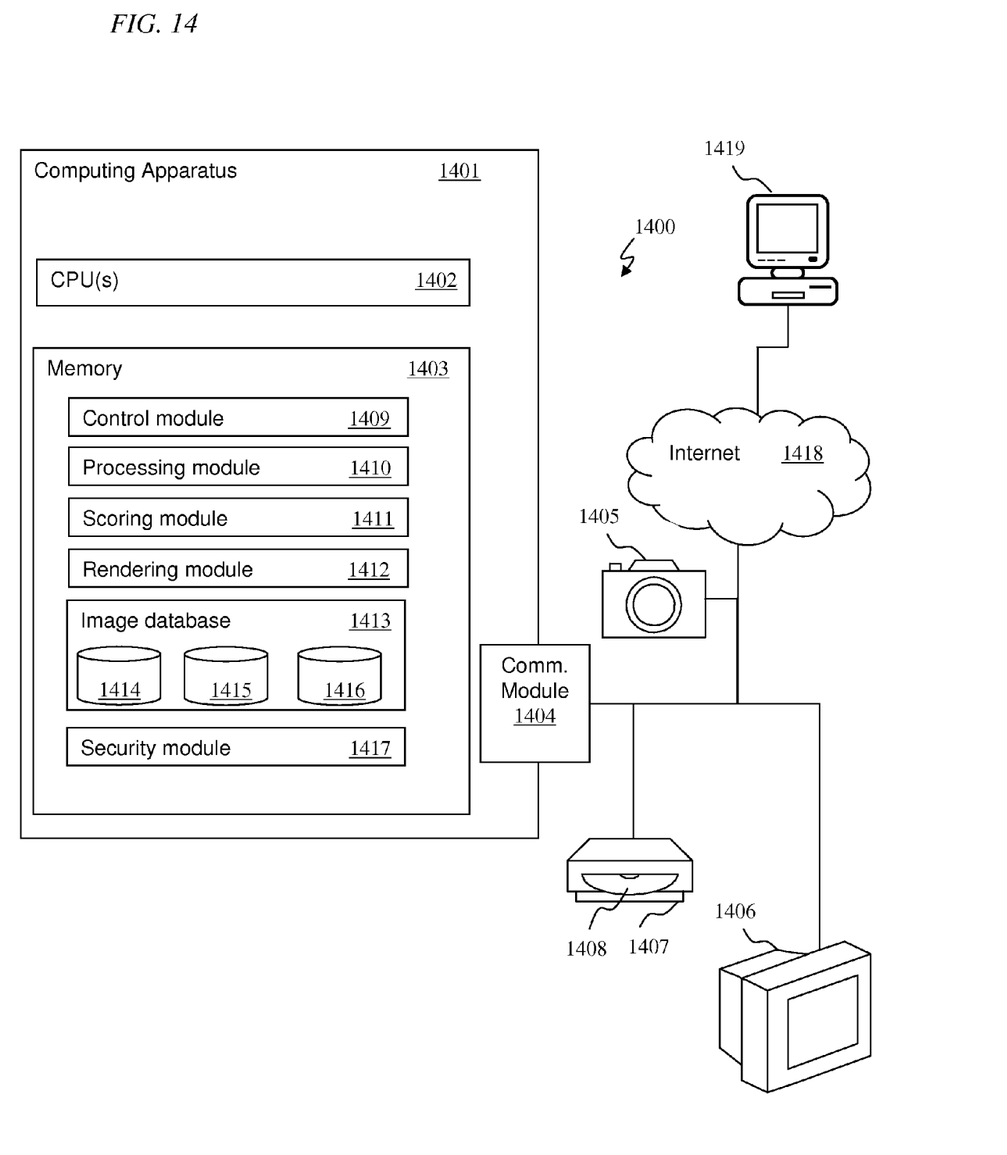
FIG. 14 illustrates a medical diagnostic comparison image generating system.

FIG. 14 illustrates a medical diagnostic comparison image generating system 1400. System 1400 comprises a computing apparatus 1401, which comprises central processing unit(s) (CPU(s)) 1402 and memory 1403, which is a non-transitory computer readable medium. CPU(s) 1402 may include a general purpose processor, a function-specific processor, such an application specific integrated circuit (ASIC) or a programmed field programmable gate array (FPGA), or multiple ones of these. Memory 1403, which is coupled to CPU(s) 1402, may comprise volatile memory, non-volatile memory, read only memory (ROM), random access memory (RAM), magnetic memory, optical memory, or another computer readable medium.

Computing apparatus 1401 also comprises a communication module 1404, which provides communication between CPU(s) 1402 and memory 1403, both within computing apparatus 1401, and external systems and devices. The functions of communication module 1404 can be distributed among multiple separate modules, systems or subsystems, based on the specifics of the input/output technologies and protocols used by computing apparatus 1401. Several external systems are illustrated in system 1400, including image collection system 1405, video display 1406, and optical drive 1407. Image collection system 1405 may be an x-ray system an MRI system, or another system that can collect medical diagnostic imagery. Video display 1406 is suitable for displaying images to a medical professional, including the baseline images and comparison images. Optical drive 1407 is illustrated as holding optical disk 1408, which is a computer readable optical medium. Optical disk 1408 may contain a patient's prior medical diagnostic images, one or more of which may be compared with a new image collected by image collection system 1405.

Multiple computational modules and data sets are illustrated within memory 1403, although it should be understood that computation and data storage could be distributed among multiple computational nodes. Memory 1403 comprises a control module 1409, which provides a GUI for a human operator to manually select and adjust images and otherwise control the comparison image generation process, for example indicating a region of interest. Memory 1403 also comprises a processing module 1410. Processing module 1410 may provide some or all of the functionality described for processing modules 1302 and 1304, pixel comparison and adjustment control module 1305, and anomaly suppression module 1306 of FIG. 13. Scoring module 1411 and rendering module 1412 are also within memory 1403, in the illustrated embodiment. Rendering module 1412 takes in the pixel matrices or adjusted baseline images, and outputs the comparison image suitable for display on video display 1406. Some of the modules thus described may be located at remote node 1419.

Image database 1413, illustrated as within memory 1403, stores prior medical diagnostic images for the patient, and may read from or write to optical drive 1407. Images may also be stored in image database 1413 or at remote node 1419. The images should have auxiliary data that includes patient identification and a timestamp, so that a medical professional, with the assistance of scoring module 1411, can identify whether a particular change is normal or abnormal for a particular lapse in time between collecting the baseline images used to generate a comparison image. As illustrated, three lower level databases 1414-1416, within the larger image database 1413, reflect the presence of image sets for three different patients, although a different database hierarchy could be used. A security module 1417 enables a secure, authenticated session over internet 1418, to which computing apparatus 1401 is connected, in the event that any image data is to be retrieved from or sent to a remote node, for example remote node 1419 or another remote node.

Apparatus 1401 is thus configured for generating a medical diagnostic comparison image, based on multiple baseline medical diagnostic images. A composite comparison image generation module, which is a combination of at least modules 1409-1412 and 1417, is comparable in function to the composition of previously-described comparison and adjustment control module 1305 and anomaly suppression module 1306 in FIG. 13. The required functions can be distributed and function can be allocated in multiple ways. These composite modules are configured to receive a first baseline medical diagnostic image and a second baseline medical diagnostic image from database 1413; operate on the first baseline medical diagnostic image and the second baseline medical diagnostic image as matrices of pixel intensity values; adjust a rotation of at least a portion of one of the baseline medical diagnostic images relative to the other baseline medical diagnostic image; adjust a magnification of at least a portion of one of the baseline medical diagnostic images relative to the other baseline medical diagnostic image; adjust a horizontal displacement of at least a portion of one of the baseline medical diagnostic images relative to the other baseline medical diagnostic image; adjust a vertical displacement of at least a portion of one of the baseline medical diagnostic images relative to the other baseline medical diagnostic image; adjust an intensity of at least a portion of one of the baseline medical diagnostic images relative to the other baseline medical diagnostic image; create a predominantly intensity-only comparison image with a region of pixel intensity difference between the first baseline medical diagnostic image and the second baseline medical diagnostic image, as processed, having a different hue than a predominant hue of the comparison image; and render the comparison image for display on video display 1406.

Apparatus 1401 comprises a scoring module 1411, which is configured to calculate a score for the comparison image, based on differences between the first baseline medical diagnostic image and the second baseline medical diagnostic image, as processed. This is similar in function to scoring module 1310 of FIG. 13. A composite comparison image generation module, coupled to or including a scoring module, may be further configured to iteratively adjust rotation, magnification, horizontal displacement, vertical displacement, and intensity of at least a portion of one of the baseline medical diagnostic images relative to the other baseline medical diagnostic image, in order to minimize a calculated score. It should be understood that minimizing a score could comprise finding a local minimum for the score, rather than finding the global minimum. This is because some optimization methods known in the art, for example genetic algorithms, which may be used with the teachings herein, may render a search for a global extremum computationally prohibitive. One optional method that may be used, and which is more likely to find a global extremum for a multi-parameter problem, is a sparse sampling of the parameter space, followed by a multi-dimensional interpolation, a search within the interpolated data set for the extremum, and then fine sampling in the neighborhood of the identified extremum candidate.

Figure 15:
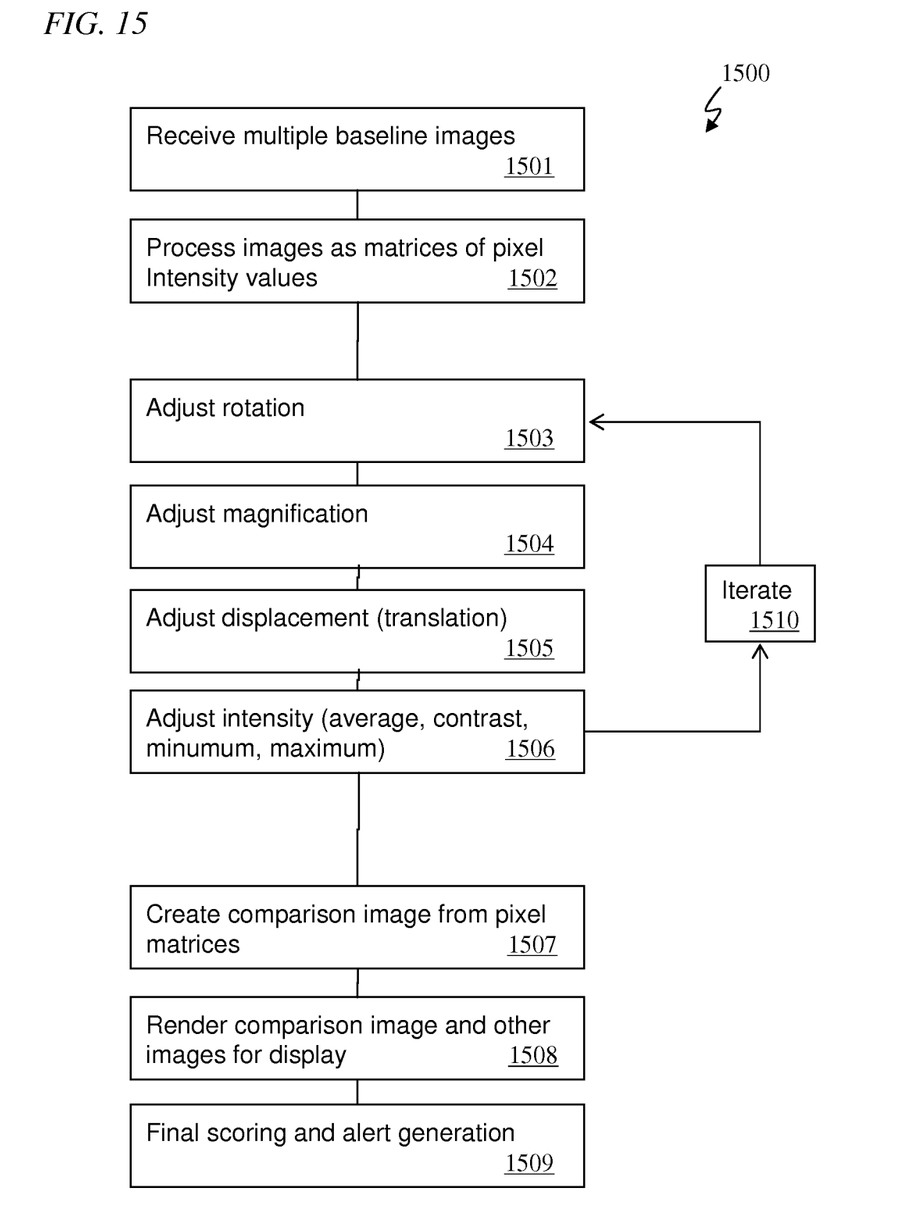
FIG. 15 illustrates a method of generating a medical diagnostic comparison image.

FIG. 15 illustrates a method 1500 of generating a medical diagnostic comparison image. Method 1500 is a computer-implemented method, implemented in code that is embodied on a computer readable medium and is configured to be executed on a processor. Method 1500 comprises the following processes: receiving a first baseline medical diagnostic image and a second baseline medical diagnostic image into a computer readable medium, box 1501; operating on the first baseline medical diagnostic image and the second baseline medical diagnostic image as matrices of pixel intensity values, box 1502; adjusting a rotation of at least a portion of one of the baseline medical diagnostic images relative to the other baseline medical diagnostic image, box 1503; adjusting a magnification of at least a portion of one of the baseline medical diagnostic images relative to the other baseline medical diagnostic image, box 1504; adjusting a displacement of at least a portion of one of the baseline medical diagnostic images relative to the other baseline medical diagnostic image, box 1505; adjusting an intensity of at least a portion of one of the baseline medical diagnostic images relative to the other baseline medical diagnostic image, box 1506; and creating a predominantly intensity-only comparison image, box 1507. In the comparison image, a region of pixel intensity difference between the first baseline medical diagnostic image and the second baseline medical diagnostic image, as processed, has a different hue than a predominant hue of the comparison image.

Method 1500 also comprises rendering the comparison image on a video display, box 1508; calculating a score for the comparison image, based on differences between the first baseline medical diagnostic image and the second baseline medical diagnostic image, as processed, box 1509; and iteratively adjusting image parameters to minimize the score, loop 1510. During the processing thus described, the matrices (or images, if the matrices are retained in an image format during processing) may be cropped, expanded and replaced with the values that result values from different process stages. For example, the process stages of {adjusting a rotation of at least one of the baseline pixel matrices relative to the other baseline pixel matrix} and {adjusting a magnification of at least one of the baseline pixel matrices relative to the other baseline pixel matrix} do not necessarily operate o the same set of two or three matrices. A set of two matrices (or images) could be input to the process stage of {adjusting a rotation of at least one of the baseline pixel matrices relative to the other baseline pixel matrix}, and the output of this stage is a second set of two matrices, perhaps of different sizes, due to cropping. Then this output set is input to the process stage of adjusting a magnification of at least one of the baseline pixel matrices relative to the other baseline pixel matrix. It should be understood that many different programming styles and implementations can be used that incorporate the inventive aspects of the teachings contained herein, and are differently optimized for computing efficiency. Therefore the subject matter of the claims is not intended to be limited to a single, unchanging set of matrices processed as described in the teachings herein, and remaining in an unchanging location in a commuter memory. Rather the claims should be interpreted to include the substitution of one matrix for another in the various process stages, so long as the substituted matrix contains the relevant information derived from the earlier matrix.

If a medical services provider asserts, or allows an agent or legal representative to assert on the provider's behalf, that the teachings contained herein are obvious as of the priority date of this Application for Patent and acknowledges that the teachings contained herein can improve the quality of medical care for that provider's patients, but yet had not attempted to avail itself of these teachings as of the date they allegedly became obvious, then that medical services provider is effectively admitting to willfully foregoing the use of an obvious improvement in the quality of medical care. Although Applicant would disagree that the teachings herein are obvious, an assertion of obviousness by medical services provider, without a corresponding attempt to use the allegedly obvious teachings, becomes an admission that the medical services provider preferred risking medical malpractice as an alternative to practicing an obvious improvement in providing medical care.

Although the invention and its advantages have been described herein, it should be understood that various changes, substitutions and alterations can be made without departing from the spirit and scope of the claims. Moreover, the scope of the application is not intended to be limited to the particular embodiments described in the specification. As one of ordinary skill in the art will readily appreciate from the disclosure, alternatives presently existing or developed later, which perform substantially the same function or achieve substantially the same result as the corresponding embodiments described herein, may be utilized. Accordingly, the appended claims are intended to include within their scope such alternatives and equivalents.

What is claimed is:

1. A computer implemented method for generating a medical diagnostic comparison image, based on multiple baseline medical diagnostic images, the method comprising:
    receiving a first baseline medical diagnostic image into a computer readable medium;
    creating a first baseline pixel matrix, wherein the first baseline pixel matrix represents an intensity of pixels in at least a portion of the first baseline medical diagnostic image;
    receiving a second baseline medical diagnostic image into the computer readable medium;
    creating a second baseline pixel matrix, wherein the second baseline pixel matrix represents an intensity of pixels in at least a portion of the second baseline medical diagnostic image;
    adjusting a rotation of at least one of the baseline pixel matrices relative to the other baseline pixel matrix;
    adjusting a magnification of at least one of the baseline pixel matrices relative to the other baseline pixel matrix;
    adjusting a displacement of at least one of the baseline pixel matrices relative to the other baseline pixel matrix;
    adjusting an intensity of at least a portion of one of the baseline pixel matrices relative to a corresponding portion of the other baseline pixel matrix;
    creating a comparison image with the first baseline pixel matrix providing a first color information and the second baseline pixel matrix providing a second color information, such that pixels in the comparison image, that correspond to pixels in the first baseline pixel matrix exceeding an intensity of corresponding pixels in the second baseline pixel matrix, have a hue of the first color, and pixels in the comparison image, that correspond to pixels in the second baseline pixel matrix exceeding an intensity of corresponding pixels in the first baseline pixel matrix, have a hue of the second color.

2. The method of claim 1 wherein the comparison image is predominantly a grayscale image.

3. The method of claim 1 wherein adjusting a rotation of a baseline pixel matrix comprises:
    generating a new pixel matrix using a method selected from the list consisting of:
        a nearest neighbor method, a linear interpolation method, and a polynomial interpolation method; and
    replacing the baseline pixel matrix with the new pixel matrix.

4. The method of claim 1 wherein adjusting a displacement of a baseline pixel matrix comprises:
    generating a new pixel matrix based on a cropped version of the baseline pixel matrix; and replacing the baseline pixel matrix with the new pixel matrix.

5. The method of claim 1 further comprising:
displaying the comparison image.

6. The method of claim 5 further comprising:
displaying at least a portion of the first baseline medical diagnostic image, in an original or processed state, simultaneously with displaying the comparison image.

7. The method of claim 6 further comprising:
displaying at least a portion of the second baseline medical diagnostic image, in an original or processed state, simultaneously with displaying at least a portion of the first baseline medical diagnostic image and the comparison image.

8. The method of claim 1 further comprising:
comparing a region of pixel intensity difference to both an average intensity difference threshold and a minimum dimension threshold; and
responsive to the region of pixel intensity difference meeting or exceeding the average intensity difference threshold and the minimum dimension threshold, causing an alert.

9. The method of claim 1 further comprising:
calculating a score for the comparison image, using one value selected from the list consisting of:
a dimension of a difference region that meets or exceeds an average intensity difference threshold; a count of difference regions that meet or exceed an average intensity difference threshold and a minimum dimension threshold; and a time difference associated with the images.

10. The method of claim 1 further comprising:
receiving a third baseline medical diagnostic image into the computer readable medium;
creating a third baseline pixel matrix, wherein the third baseline pixel matrix represents an intensity of pixels in at least a portion of the third baseline medical diagnostic image;
adjusting a rotation of the third baseline pixel matrices relative to the other baseline pixel matrices;
adjusting a magnification of the third baseline pixel matrices relative to the other baseline pixel matrices;
adjusting a displacement of the third baseline pixel matrices relative to the other baseline pixel matrices;
adjusting an intensity of at least a portion of the third baseline pixel matrices relative to corresponding portions of the other baseline pixel matrices;
wherein creating a comparison image comprises creating a predominantly intensity-only image with the third baseline pixel matrix providing a third color information.

11. The method of claim 1 further comprising:
receiving from a graphical user interface (GUI) an indication of a region of interest, wherein creating a comparison image comprises creating an image that illustrates the region of interest.

12. A computer program embodied on a computer executable medium and configured to be executed by a processor, the program comprising:
code for receiving a first baseline medical diagnostic image and a second baseline medical diagnostic image into a computer readable medium;
code for operating on the first baseline medical diagnostic image and the second baseline medical diagnostic image as matrices of pixel intensity values;
code for adjusting a rotation of at least a portion of one of the baseline medical diagnostic images relative to the other baseline medical diagnostic image;
code for adjusting a magnification of at least a portion of one of the baseline medical diagnostic images relative to the other baseline medical diagnostic image;
code for adjusting a displacement of at least a portion of one of the baseline medical diagnostic images relative to the other baseline medical diagnostic image;
code for adjusting an intensity of at least a portion of one of the baseline medical diagnostic images relative to the other baseline medical diagnostic image;
code for creating a predominantly intensity-only comparison image with a region of pixel intensity difference between the first baseline medical diagnostic image and the second baseline medical diagnostic image, as processed, having a different hue than a predominant hue of the comparison image; and
code for rendering the comparison image on a video display.

13. The computer program of claim 12 wherein the comparison image is predominantly a grayscale image.

14. The computer program of claim 12 further comprising:
code for calculating a score for the comparison image, based on differences between the first baseline medical diagnostic image and the second baseline medical diagnostic image, as processed.

15. The computer program of claim 14 further comprising:
code for iteratively adjusting rotation, magnification, horizontal displacement, vertical displacement, and intensity of at least a portion of one of the baseline medical diagnostic images relative to the other baseline medical diagnostic image, in order to minimize the score.

16. An apparatus for generating a medical diagnostic comparison image, based on multiple baseline medical diagnostic images, the apparatus comprising:
a processor;
a computer readable medium coupled to the processor, the computer readable medium comprising:
a database of medical diagnostic images; and
a comparison image generation module configured to:
receive a first baseline medical diagnostic image and a second baseline medical diagnostic image from the database;
operate on the first baseline medical diagnostic image and the second baseline medical diagnostic image as matrices of pixel intensity values;
adjust a rotation of at least a portion of one of the baseline medical diagnostic images relative to the other baseline medical diagnostic image;
adjust a magnification of at least a portion of one of the baseline medical diagnostic images relative to the other baseline medical diagnostic image;
adjust a displacement of at least a portion of one of the baseline medical diagnostic images relative to the other baseline medical diagnostic image;
adjust an intensity of at least a portion of one of the baseline medical diagnostic images relative to the other baseline medical diagnostic image;
create a predominantly intensity-only comparison image with a region of pixel intensity difference between the first baseline medical diagnostic image and the second baseline medical diagnostic image, as processed, having a different hue than a predominant hue of the comparison image; and
render the comparison image for display on a video display.

17. The apparatus of claim 16 further comprising:
a scoring module embodied on a computer readable medium coupled to the processor, the scoring module configured to calculate a score for the comparison image, based on differences between the first baseline medical diagnostic image and the second baseline medical diagnostic image, as processed.

18. The apparatus of claim 17 wherein the comparison image generation module is further configured to iteratively adjust rotation, magnification, horizontal displacement, vertical displacement, and intensity of at least a portion of one of the baseline medical diagnostic images relative to the other baseline medical diagnostic image, in order to minimize the score.

* * * * *